United States Patent [19]

Kanda

[11] Patent Number: 5,154,176
[45] Date of Patent: Oct. 13, 1992

[54] LIVER FUNCTION TESTING APPARATUS

[75] Inventor: Masahiko Kanda, Osaka, Japan

[73] Assignee: Sumitomo Electric Industries, Ltd., Osaka, Japan

[21] Appl. No.: 800,865

[22] Filed: Nov. 26, 1991

Related U.S. Application Data

[63] Continuation of Ser. No. 406,310, Sep. 12, 1989, abandoned.

[30] Foreign Application Priority Data

Sep. 14, 1988 [JP] Japan .............................. 63-230790

[51] Int. Cl.⁵ ............................................... A61B 5/00
[52] U.S. Cl. ..................................... 128/633; 128/665
[58] Field of Search ................ 128/632, 633, 665, 666

[56] References Cited

U.S. PATENT DOCUMENTS

| | | | |
|---|---|---|---|
| 3,677,648 | 7/1972 | Dorsch | 128/666 |
| 4,608,990 | 9/1986 | Elings | 128/666 |
| 4,805,623 | 2/1989 | Jobsis | 128/633 |
| 4,832,484 | 5/1989 | Aoyagi et al. | 128/633 |
| 4,848,349 | 7/1989 | Sherman et al. | 128/633 |
| 4,905,703 | 3/1990 | Kanda | 128/666 |

FOREIGN PATENT DOCUMENTS 0276477  8/1988  European Pat. Off. .

OTHER PUBLICATIONS

Durov et al, "Instrument for Measuring Microconcentrations of Indicator Dyes in Blood", Biomed. Eng. (USA) vol. 12, No. 1 (Jan.-Feb. 1978).

Primary Examiner—Ruth S. Smith
Attorney, Agent, or Firm—W. G. Fasse; D. H. Kane, Jr.

[57] ABSTRACT

A liver function testing apparatus measures n-times the values $\Delta \log T_1$ and $\Delta \log T_2$ corresponding to pulse wave signals obtained upon passage through a prescribed optical path in vital tissue. A sensor (30) having first and second light sources (3, 4) and a light receiving element (6) is attached to a testee (5) before injection of a specific dye. A value $\alpha_0$ is calculated by using a statistical computation with two variables as to n $\Delta \log T_1$ and $\Delta \log T_2$ on the basis of an equation of $\Delta \log T_1 = \alpha_0 \cdot \Delta \log T_2 . \Delta \log T_1$ and $\Delta \log T_2$ corresponding to pulse wave signals are measured in response to intensity levels of first light and second light passing through the vital tissue during a prescribed time following an injection on the basis of decision outputs representing levels of the first light and the second light from the light sources after the specific dye is injected. A value Cg corresponding to a specific dye concentration in the blood is calculated from $\alpha_0$, $\Delta \log T_1$ and $\Delta \log T_2$. A simulation curve as a function of time changes of the result of the measurements is calculated by the application of the least squares method, thereby to obtain a blood plasma disappearance rate K and a T-minute retention rate R % of the specific dye on the basis of the simulation curve.

4 Claims, 3 Drawing Sheets

LIVER FUNCTION TESTING APPARATUS

This application is a continuation of application Ser. No. 07/406,310 Sep. 12, 1989, now abandoned.

FIELD OF THE INVENTION

The present invention relates to a liver function testing apparatus. More specifically, the invention relates to a liver function testing apparatus for automatically performing measurements for testing and diagnosing the function of a liver by injecting a specific dye, which is selectively taken in and removed only by the liver. The dye is injected into a person's blood and a blood plasma disappearance rate and a plasma retention rate are measured.

BACKGROUND INFORMATION

In general, the blood plasma disappearance rate and the retention rate have been measured by a known method of blood sampling through use of indocyanine green (hereinafter referred to as ICG) serving as a specific dye.

According to said known method, a tester intravenously injects ICG into an elbow vein of a person to be tested. Blood samples are taken from the testee three times after 5, 10 and 15 minutes have elapsed counted from the injection. Upon coagulation of blood clots in the blood samples, the blood serum is separated and the absorbance is measured at a wavelength of 805 nm by a spectrophotometer to obtain ICG concentration values in the blood serum after 5, 10 and 15 minutes have elapsed. The measured values are compared to a previously obtained calibration curve plotted as the ICG concentration in the blood as a function of the absorbance. The blood plasma disappearance rate and the retention rate are calculated from changes of the concentration values. ICG is dissolved in a physiological salt solution or the like. The repeated taking of blood samples subjects the patient to mental and physical burdens which are undesirable. Japanese Patent Publication Gazette No. 58649/1985 discloses a method of applying light through the body surface of an organism and measuring quantities of light of a wavelength having a high ICG absorption sensitivity and that of a wavelength substantially having no such a sensitivity, whereby the blood plasma disappearance rate and the retention rate are obtained from changes occurring with the passage of time as shown in a dye disappearance curve, without performing blood sampling.

An $R_{MAX}$ measuring method for evaluating the blood plasma disappearance rate requires performing measurements several times with changes in the ICG dosages. Such a method has been widely employed in recent years, even though blood samples must be taken ten or more times, which further increase the burdens on the testee.

In the aforementioned method of performing measurements without blood sampling, which is disclosed in Japanese Patent Publication Gazette No. 58649/1985 or Japanese Patent Laying-Open Gazette No. 162934/1986, the output of a sensor actually attached to an organism, fluctuates due to such influences as a blood flow disturbance caused by compressing a blood vessel, vibration of the organism, which is the object of measurement, pulsation in the organism, changes of the blood volume in the organism, and the like. The blood volume is changed, for example, by merely vertically moving an arm. As a result, a correct dye disappearance curve cannot be obtained. Thus, the blood plasma disappearance rate and the retention rate obtained by the curve cannot be recognized as being correct.

Further, there is disclosed a method of measuring the ICG concentration in blood by employing the widths between peaks of changes in the quantities of light beams of two wavelengths caused by pulse waves through an optical blood measuring apparatus described in Japanese Patent Laying-Open Gazette No. 128387/1975 or an oximeter described in Japanese Patent Laying-Open Gazette No. 88778/1978 as another method of performing measurements without blood sampling. However, such widths of changes in the light quantities cannot be correctly measured due to vibration of the organism, etc., and it has been impossible to obtain a correct dye disappearance curve.

SUMMARY OF THE INVENTION

Accordingly, it is a principal object of the present invention to provide a liver function testing apparatus which remains uninfluenced by such factors, as blood flow disturbance, vibration of an organism, pulsation in the organism and changes of the blood volume in the organism caused while a sensor is attached to the organism, to enable a correct measurement. Briefly stated, a sensor comprising light sources and a light receiving element, is attached to a testee before the testee receives an injection of a specific dye. The sensor measures values $\Delta \log T_1$ and $\Delta \log T_2$ corresponding to pulse wave signals obtained when the testee's blood passes through a prescribed optical path in the vital tissue to which the sensor is attached. The measurements are made n-times. Prior to a dye injection a value $\alpha_0$ is calculated by statistical computation using two variables, namely n values of $\Delta \log T_1$ and n values of $\Delta \log T_2$ and further using the following operation expression:

$$\Delta \log T_1 = \alpha_0 \cdot \Delta \log T_2 \rightarrow \alpha_0 = \Delta \log T_1 / \Delta \log T_2.$$

The computations are made in response to decision outputs of levels of respective light beams emitted by the light sources. The values $\Delta \log T_1$ and $\Delta \log T_2$ corresponding to the pulse wave signals are measured on the basis of light intensity levels of first light and second light reflected by the vital tissue. The measurements are made during a time span beginning when the injection is completed and ending when a prescribed length of time after the specific dye injection has elapsed. A value Cg corresponding to a specific dye concentration in the blood, is derived or calculated from $\alpha_0$, $\Delta \log T_1$ and $\Delta \log T_2$. Additionally, a function or a simulation curve representing calculation results changing with time is calculated by the least squares method for fitting output calculation results of a blood plasma disappearance rate K and a T-minute retention rate R % of the specific dye to the simulation curve or function.

According to the present invention, therefore, the time management of a correct specific dye disappearance curve becomes possible, whereby correct data can be obtained. Further, the blood plasma disappearance rate K and the T-minute retention rate R % can be obtained, not from several samples taken according to the conventional blood sampling method, but from a large number of plasma disappearance curve data, thereby improving the reliability of the data. In addition, the present method can be further simplified as compared with the conventional testing method of obtaining the blood plasma disappearance rate K and the T-minute retention rate R %, by performing the measurements three times with changes of the ICG dosages. Further, the problematic influences such as blood flow disturbance, vibration of an organism, pulsation in the organism and changes of the blood volume in the organism caused upon attachment of a sensor to the organism, can be avoided to enable a correct measurement. Thus, the present invention is effectively applicable to the general field of measuring a dye in an organism without any invasion of the organism for taking blood samples.

In a preferred embodiment of the present invention $\Delta \log T_1$ and $\Delta \log T_2$ are measured n times as operation values $Cg(T)$, assuming that $\Delta \log T_1$ and $\Delta \log T_2$ represent values corresponding to pulse wave signals of intensity levels of a first light and a second light passing through a prescribed optical path in a vital tissue, and that a value $\alpha(t)$ is evaluated as $n \times 2$ by a statistical computation with two variables according to $\Delta \log T_1 = \alpha(t)$. $\Delta \log T_2$, to obtain $Cg(t) = \beta(\alpha(t) - \alpha_0)$ wherein B is a constant.

In the preferred embodiment, further, the function Cg of the calculated simulation curve is:

$$C_g = A \cdot e^{Bt}$$

where
Cg: the calculated value
t: elapsed time (min.) after injection of the specific dye
A, B: constants The blood plasma disappearance rate K and the T-minute retention rate R % are obtained from:

$$K = -B$$

$$R \% = e^{Bt}$$

assuming that the elapsed time after injection, which characteristically expresses intake of the specific dye in the liver, is T expressed in minutes.

These and other objects, features, aspects and advantages of the present invention will become more apparent from the following detailed description of the present invention when taken in conjunction with the accompanying drawings.

DESCRIPTION OF THE PREFERRED EMBODIMENT

Figure 2:
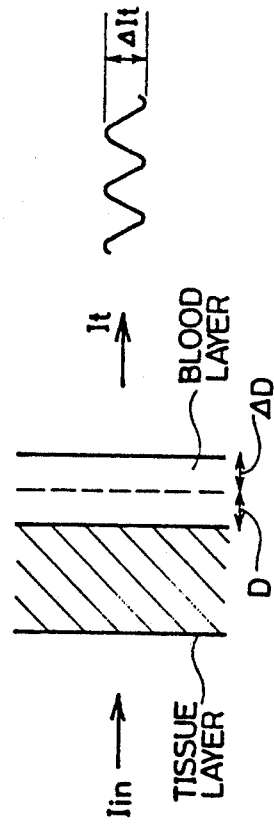
FIG. 2 illustrates incident light applied to an organism and light transmitted through the organism.
Figure 3:
FIG. 3 illustrates changes in the quantity of light corresponding to a pulse wave.
Figure 4:
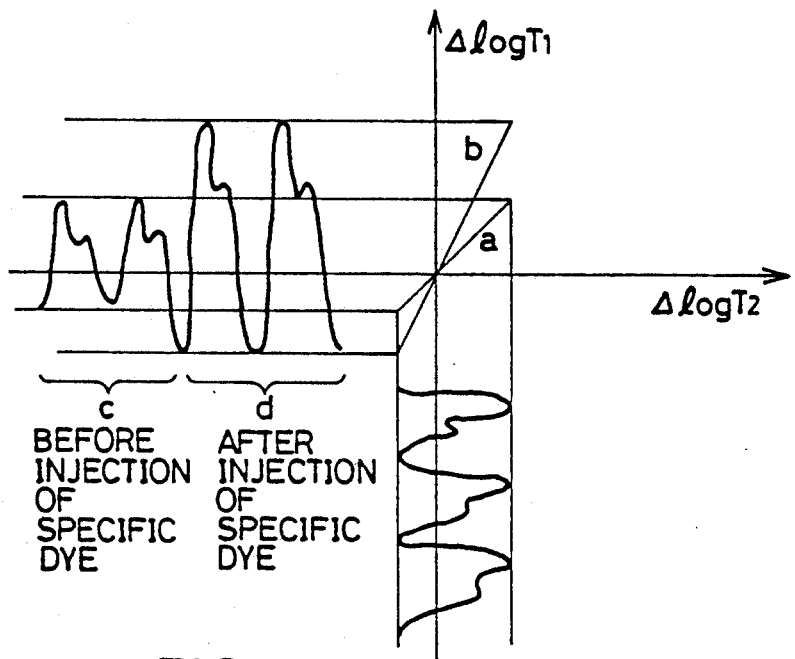
FIG. 4 illustrates changes of $\Delta \log T_1$ and $\Delta \log T_2$ expressed on x and y coordinates.

FIG. 2 illustrates incident light $I_{in}$ which is applied to vital tissue and transmitted light $I_t$, FIG. 3 illustrates changes in the quantity of transmitted light corresponding to a pulse wave, and FIG. 4 illustrates changes of $\Delta \log T_1$ and $\Delta \log T_2$ expressed on x and y coordinates.

With reference to FIGS. 2 to 4, the principle of the present invention will now be described. When incident light $I_{in}$ is applied to an organism as shown in FIG. 2, the absorbance A is expressed as $\log I_t/I_{in}$, assuming that It represents the quantity of transmitted light. The organism is formed by a tissue layer and a blood layer as shown in FIG. 2, and the blood layer is formed by an arterial layer and a venous layer. The thickness of the arterial layer is changed by $\Delta D$ in response to pulsation (pulse wave) caused by the heart. The quantity $I_t$ of the transmitted light varies with this change. Therefore, the absorbance A is similarly changed by $\Delta A$. Hence, $$\Delta A = \Delta \log I_t \tag{1}$$

Assuming that $\Delta A_1$ and $\Delta A_2$ represent changes of absorption quantities caused by pulse waves of a wavelength $\lambda_1$ largely absorbed by a specific dye and an unabsorbed wavelength $\lambda_2$, $\Delta A_1$ and $\Delta A_2$ are expressed as: (after dye injection)

$$\Delta A_1 = (E_\beta^1 \cdot C_\beta + E_g^1 \cdot c_g) \cdot \Delta D \text{ and} \tag{2}$$

$$\Delta A_2 = E_\beta^2 \cdot C_\beta \cdot \Delta D, \tag{3}$$

where
$E_\beta^1$: is the absorption coefficient of blood at light wavelength $\lambda_1$,
$E_\beta^2$: is the absorption coefficient of blood at light wavelength $\lambda_2$,
$E_g^1$: is the absorption coefficient of ICG at light wavelength $\lambda_1$
$C_\beta$: is the blood concentration
$C_g$: is the specific dye concentration, and
$\Delta D$ : is the change in thickness of the blood layer.

However, before dye injection the addend in equation (2) is zero. Therefore, equation (2) may be expressed as follows:

$$\Delta A_1 = E_\beta^1 \cdot C_\beta \cdot \Delta D. \tag{4}$$

Additionally, the degree of oxygen saturation during testing of the blood is assumed to be constant. Therefore, and because the above defined value $\alpha_0$ correslates $\Delta A_1$ and $\Delta A_2$ we can write equation (5)

$$E_\beta^1 \cdot C_\beta \cdot \Delta D = \alpha_0 (E_\beta^2 \cdot C_\beta \cdot \Delta D) \tag{5}$$

based on equations (3) and (4). Solving equation (5) for $\alpha_0$ or $E_\beta^1$ we obtain:

$$\alpha_0 = \frac{E_\beta^1}{E_\beta^2} \rightarrow E_\beta^1 = \alpha_0 E_\beta^2. \tag{6}$$

Inserting equation (6) into equation (4), we obtain for
$$\Delta A_1 = \alpha_0 E_\beta^3 C_\beta \cdot \Delta D \tag{7}$$

According to equation (3) the factor $E_\beta^2 \cdot C_\beta \cdot \Delta D$ equals $\Delta A_2$. Hence, inserting $\Delta A_2$ into equation (7), we obtain, before dye injection:
$$\Delta A_1 = \alpha_0 \Delta A_2 \tag{8}$$

After dye injection, the addend of equation (2) must be added to equation (8), thus:
$$\Delta A_1 = \alpha_0 \Delta A_2 + E_g^1 \cdot C_g \cdot \Delta D \tag{9}$$

Dividing both sides of equation (9) by $\Delta A_2$, having regard to equation (3), we obtain:

$$\frac{\Delta A_1}{\Delta A_2} = \alpha_0 + \frac{E_g^1 \cdot C_g}{E_\beta^2 \cdot C_\beta} \quad (10)$$

Solving equation (10) for $C_g$, we obtain:

$$C_g = \left(\frac{\Delta A_1}{\Delta A_2} - \alpha_0\right) \frac{E_\beta^2 C_\beta}{E_g^1} \quad (11)$$

Since $E_\beta^1$ and $E_g^1$ in equation (11) are known physical values, and $C_\beta$ is assumed to be constant, the expression $E_\beta^2 C_\beta/E_g^1$ is also a constant value which is the above mentioned $\beta$.

Hence, the specific dye concentration $C_g$ in the blood can be calculated by obtaining $\Delta A_1/\Delta A_2$ after injection of the specific dye.

Assuming that $T_1$ and $T_2$ represent quantities of transmitted light having the wavelength $\lambda_1$ and the wavelength $\lambda_2$ respectively, while $\Delta T_1$ and $\Delta T_2$ represent changes thereof caused by $\Delta D$, the following equations result from the expression (1) for $\alpha_0$ and $\alpha$:

$\alpha_0 = \Delta\log T_1/\Delta\log T_2 =$, prior to dye injection, (12)

and $\alpha = \Delta A_1/\Delta A_2 = \Delta\log T_1(i)/\Delta\log T_2(i)$, after dye injection (13), as will be explained in more detail below.

Hence, the expression (8) is solved to obtain $\alpha_0$ before injection of the specific dye and the expression (13) is solved to obtain $\alpha$ after injection of the specific dye. $C_g$ is calculated from the expression (11). In the oximeter described in the aforementioned Japanese Patent Laying-Open Gazette No. 88778/1978 etc., the difference between peaks of changes in quantity of light corresponding to a pulse wave, has been regarded as $\Delta\log T_1$, as shown in FIG. 3. However, this method can only prepare a sample corresponding to the cardiac cycle, and the above $\Delta\log T_1$ has been obtained by performing the measurement several times and averaging the results in the actual circumstances.

According to the present invention, the difference between the peaks of curves c and d in FIG. 4 is not obtained, rather $\Delta\log T_1$ is plotted on the y-axis and $\Delta\log T_2$ is plotted on the x-axis as shown in FIG. 4. Curve "c" represents values obtained through a light sensor element 6 prior to dye injection. Curve "d" represents values obtained through light sensor element 6 after dye injection. Changes in the measured values are as shown in FIG. 4, whereby a straight line "a" has an inclination $\alpha_0$ before injection of the specific dye. $\alpha_0$ is used in the above expression (6). Then, when the specific dye has been injected, the absorbance of $\lambda_1$ is changed as shown by the pulse waveform d and the inclination is changed as represented by a straight line b having an inclination $\alpha = \Delta A_1/\Delta A_2$ as shown in the above expression (6).

Hence, inclination $\alpha(t)$ can be accurately calculated by increasing the number of measurement samples of $\Delta\log T_1$ and $\Delta\log T_2$ for understanding the concentration changes of the specific dye at a high speed without depending on the cardiac cycle.

A testing apparatus for operating according to this method, will now be described.

Figure 1:
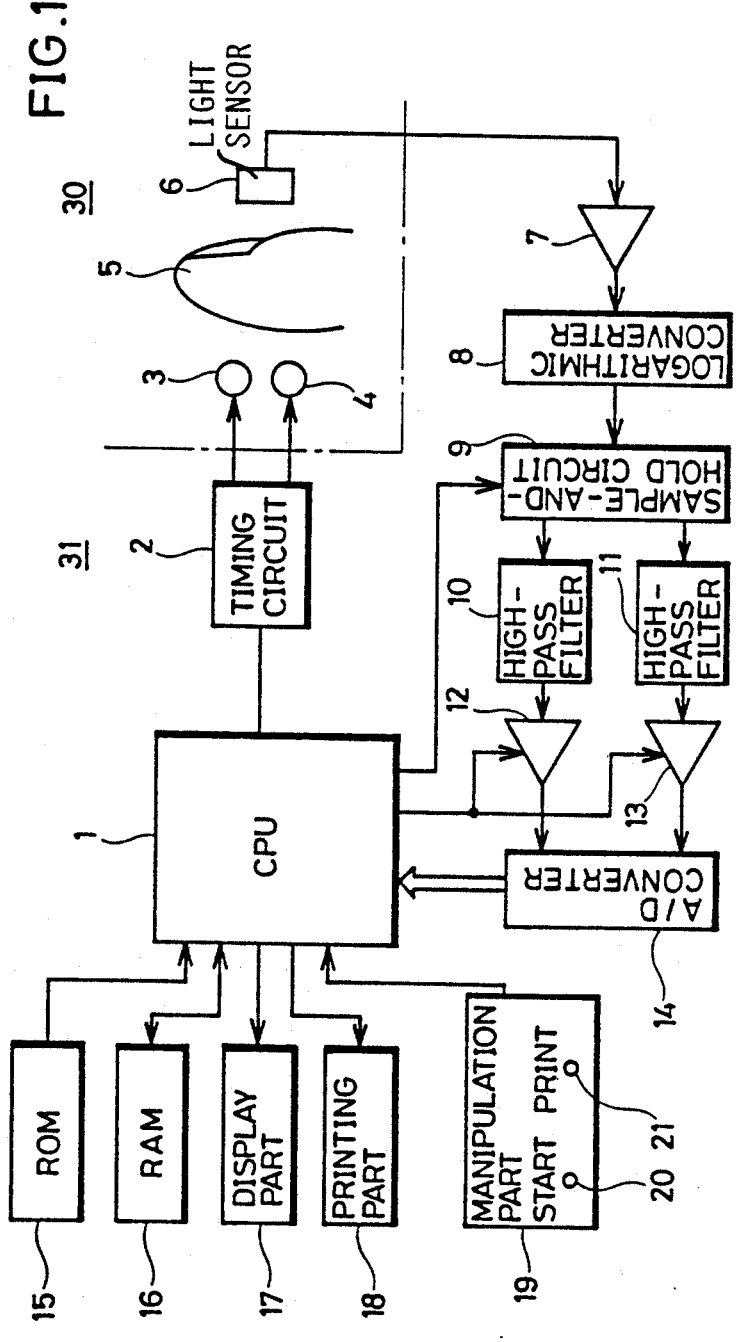
FIG. 1 is a schematic block diagram showing an embodiment of the present invention.

FIG. 1 is a schematic block diagram showing an embodiment of the present invention. Referring to FIG. 1, a liver function testing apparatus comprises a sensor section 30 and a measurement processing section 31. The sensor section 30 includes a first light source 3, a second light source 4 and a light receiving sensor element 6. The first light source 3 generates optical pulses of the wavelength $\lambda_1$ having a large absorbance with respect to the specific dye. The second light source 4 generates optical pulses of the wavelength $\lambda_2$ having no such absorbance. The light receiving sensor element 6 receives light beams, which are applied by the light sources 3 and 4 to vital tissue 5 to pass through a prescribed optical path. The light sources 3 and 4 are controlled by a timing circuit 2 on the basis of a command from a CPU 1 which is provided in the measurement processing section 31, to alternately generate the light beams in a pulse operation.

The CPU 1 included in the measurement processing section 31 serves as arithmetic means. As hereinabove described, the CPU 1 supplies prescribed pulses to the light sources 3 and 4 through the timing circuit 2. The light beams emitted by the first and second light sources 3 and 4 pass through the prescribed optical path in the vital tissue 5 to be incident upon the light receiving sensor element 6. A current generated from the light receiving sensor element 6 is subjected to a current-voltage conversion and amplified by an amplifier 7. The amplified signal is supplied to a logarithmic converter 8 for a logarithmic conversion, and supplied to a sample-and-hold circuit 9, for separating the signals in accordance with the wavelengths $\lambda_1$ and $\lambda_2$. The separated respective signals of the wavelengths $\lambda_1$ and $\lambda_2$ are supplied to high-pass filters 10 and 11. These signals include pulse wave components and blood volume changes such as those in the venous blood represented by large fluctuating or undulating components log $T_1$, log $T_2$ shown in FIG. 7. Therefore, the high-pass filters 10 and 11 remove these undulating components to output only pulsating components, which in turn are supplied to an A-D converter 14 through amplifiers 12 and 13. The amplifiers 12 and 13 are so controlled that the amplification factors thereof are changed in response to control signals from the CPU 1. The A-D converter 14 converts the inputted signals into digital signals and supplies the same to the CPU 1. The CPU 1 stores the digital signals in a RAM 16.

The CPU 1 is connected with a ROM 15, the RAM 16, a display section 17, a printing section 18 and a manipulation section 19. The ROM 15 stores programs based on flow charts shown in FIGS. 5 and 6 as hereinafter described. The manipulation section 19 includes a start key 20 and a print key 21. The start key 20 is adapted to command starting of a measurement mode, and the print key 21 is adapted to supply a command for printing out test results in the printing section 18.

Figure 7:
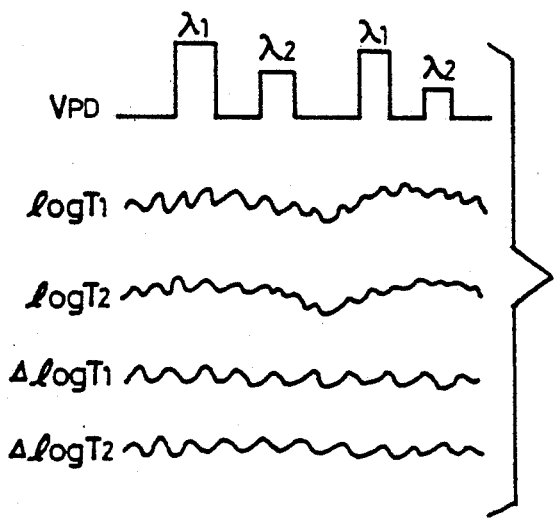
FIG. 7 is a waveform diagram showing voltages corresponding to pulse waves.
Figure 8:
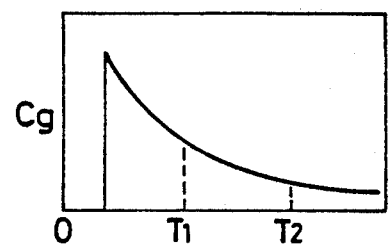
FIG. 8 illustrates an exemplary ICG disappearance curve.
Figure 5:
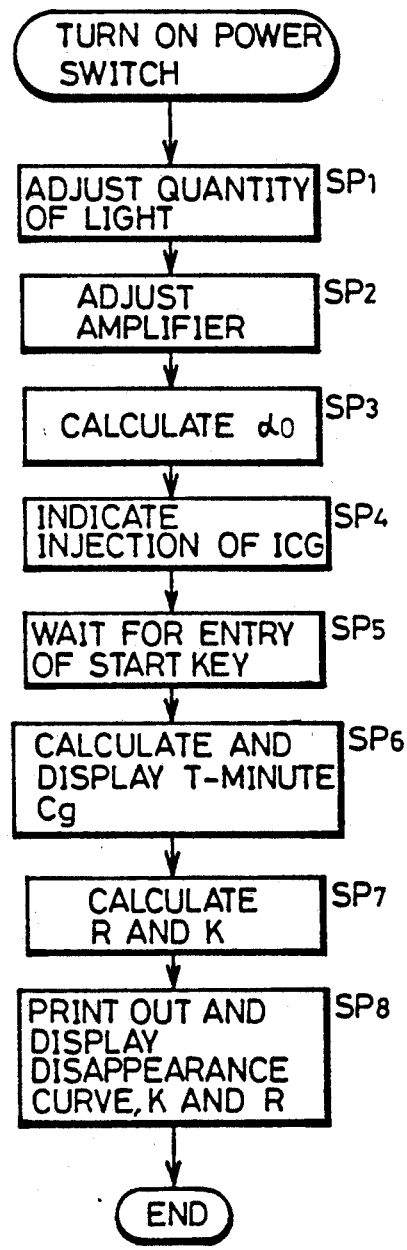
FIGS. 5 and 6 are flow charts for illustrating an actual calculation in accordance with the embodiment of the present invention.
Figure 6:
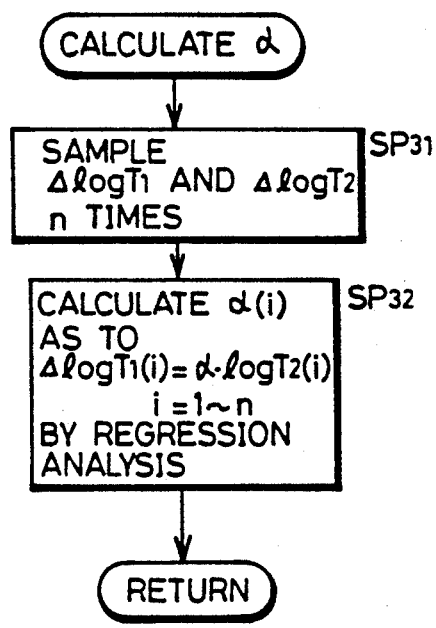

FIGS. 5 and 6 are flow charts for illustrating an actual operation of the embodiment of the present invention, FIG. 7 is a waveform diagram showing voltages corresponding to pulse waves, and FIG. 8 illustrates an exemplary ICG disappearance curve obtained when ICG is used as the specific dye.

With reference to FIGS. 1 and 5 to 8, an actual operation of the embodiment of the present invention will now be described whereby ICG is used as the specific dye. At a step SP1 shown in FIG. 5, power is applied to the apparatus and then the light quantities are adjusted. That is, the CPU 1 supplies a command to the timing circuit 2 for adjusting the driving currents for the light sources 3 and 4 respectively, while adjusting the light receiving element 6 so that its output reaches a prescribed level.

Light beams emitted by the light sources 3 and 4 pass through a prescribed optical path in the vital tissue 5 to be incident upon the light receiving element 6, and a current generated by the light receiving element 6 is subjected to a current-voltage conversion and amplified by the amplifier 7, to provide an output $V_{PD}$ shown in FIG. 7. This signal is supplied to the logarithmic converter 8 for a logarithmic conversion, and separated into signals of the waveforms $\lambda_1$ and $\lambda_2$ by the sample-and-hold circuit 9. These signals are expressed as log $T_1$ and log $T_2$ in FIG. 7 respectively. These signals contain components caused by pulse waves and by blood volume changes such as those in venous blood etc. These components fluctuate or undulate substantially and the fluctuations are removed by the high-pass filters 10 and 11 so that only pulsating components such as $\Delta\log T_1$ and $\Delta\log T_2$ shown in FIG. 7 are extracted.

At a step SP2, the CPU 1 controls the amplification factors of the amplifiers 12 and 13 for amplifying the signals until the widths between peaks of the pulse wave corresponding voltages of $\Delta\log T_1$ and $\Delta\log T_2$ shown in FIG. 7 reach certain levels. Then, the CPU 1 calculates $\alpha_0$ at a step SP3 using the above relationship $\alpha_0 = -\Delta\log T_1/\Delta\log T_2$ prior to a dye injection.

Then, the CPU 1 displays an indication such as "inject ICG", for example, on the display section 17 at a step SP4. Thus, the operator prepares to inject ICG into the vein of the organism, and turns on the start key 20 of the manipulation section 19 simultaneously with the ICG injection.

After the dye injection has been completed, CPU 1 also calculates $\alpha$ by sampling the signals of $\Delta\log T_1$ and $\Delta\log T_2$ n-times at a step SP31 as shown in FIG. 6 and by then performing a regression analysis as to $i=1$ to n by using $2\times n$ data in a calculation of $\alpha$ from $\Delta\log T_1(i) = \alpha \cdot \Delta\log T_2(i)$ at a step SP32. The calculated value of $\alpha$ is then stored in the RAM 16 in the same way as $\alpha_0$.

During step SP5 the CPU 1 waits for the operation of the start key 20. When the start key has been operated the CPU 1 calculates the T-minute ICG concentration Cg in the blood at step SP6. More specifically, $\alpha$ at a certain time t following a dye injection is evaluated in accordance with the aforementioned flow chart shown in FIG. 6, thereby to obtain Cg from the above expression (11), supposing that $\alpha$ is $\Delta A_1/\Delta A_2$. The data of Cg provide an ICG disappearance curve as shown in FIG. 8, for example, and within the data, constants A and B are evaluated in accordance with the least squares method with a simulation curve of:

$$Cg(I) = Ae^{Bt}$$

$$t = T_S/(n-1) \text{ (min.)}$$

with respect to data between times $T_1$ and $T_2$ ($0 < T_1 < T_2 < T$), whereby $T_s = T_2 - T_1$.

Then, the CPU 1 calculates a blood plasma disappearance rate $K = -B$ and a T-minute retention rate $R\% = e^{Bt}$ at a step SP7, to evaluate K and R.

Then, the CPU 1 displays the disappearance curve shown in FIG. 8 and the values K and R on the display section 17, and outputs the same to the printing section 18 to print out the same at a step SP8.

The present invention can be also applied to an apparatus for measuring $R_{MAX}$ by evaluating/calculating values K of various ICG dosages.

According to the present invention, as hereinabove described, optical pulses of a wavelength largely absorbed by a specific dye and optical pulses of a wavelength not absorbed by the same, are applied to vital tissue at prescribed levels to detect optical pulses passing through a prescribed optical path in the vital tissue, and after the specific dye is injected on the basis of the outputs, a blood plasma disappearance rate and a retention rate of the specific dye are obtained on the basis of light receiving outputs from the injection during a prescribed lapse of time in accordance with a prescribed equation. Thus, time management of a correct specific dye disappearance curve is enabled and correct data are obtained.

Further, the blood plasma disappearance rate and the retention rate are obtained without taking any blood samples as are used by the conventional blood sampling method, rather the invention uses a large number of disappearance curve data, whereby the reliability of the data is improved.

In addition, the present method of measurement can be further simplified as compared with the conventional testing method of obtaining the blood plasma disappearance rate and the retention rate by performing the measurements several times with changes in the ICG dosages.

Further, problematic or undesirable influences such as blood flow disturbances, vibration of an organism, pulsation in the organism and changes of the blood volume in the organism caused by the attachment of a sensor to the organism, are eliminated for obtaining correct measurements. Thus, the present invention is effectively applicable to the general field of measuring a dye in an organism without any invasion of the organism.

The present invention is applicable not only to a liver function testing apparatus but to an apparatus, such as a pulse oximeter, for example, for measuring changes in the concentration of a dye in an organism through pulse waves.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for testing a liver to provide liver function information, comprising
   (a) first light source means (3) for exposing vital tissue of a patient to a first light having a first wavelength ($\lambda_1$) substantially absorbed by a specific dye removable by the liver and dosed into blood flowing through said vital tissue, and second light source means (4) for exposing said vital tissue to a second light having a second wavelength ($\lambda_2$) substantially not absorbed by said specific dye,
   (b) light receiving sensor means (6) positioned for detecting said first light and said second light after passing through said vital tissue,
   (c) signal processing means for processing signals received from said light receiving sensor means,
      (c1) said signal processing means including logarithmic circuit means (8) connected for receiving light intensity values from said light receiving sensor means (6) for logarithmically converting said light intensity values ($T_1$) of said first light and ($T_2$) of said second light detected by said light receiving sensor means (6) to form logarithmic signals log $T_1$ and log $T_2$, (c2) sample and hold circuit means (9) connected to said logarithmic circuit means (8) for separating said logarithmic signals according to said first and second light wavelengths ($\lambda_1$ and $\lambda_2$), and (c3) filter means (10, 11) connected to said sample and hold circuit means (9) for setting maximum and minimum signal limits for forming signal values $\Delta$log $T_1$ and $\Delta$log $T_2$ prior to injecting said specific dye, (d) a central processing unit (CPU) connected to said signal processing means for performing arithmetic operations, (d1) said central processing unit including first arithmetic circuit means for calculating $\alpha_0$ from said signal values $\Delta$log $T_1$ divided by $\Delta$log $T_2$, said calculating being performed repeatedly as a statistical computation prior to a dye injection, (d2) timing means for indicating a time for injecting said specific dye, (d3) second arithmetic circuit means for providing signal values $\Delta$log $T_1(i)$ and $\Delta$log $T_2(i)$ during a fixed length of time following an injection of said specific dye, where i is a number from 1 to n, (d4) third arithmetic circuit means for calculating $\alpha$ from said signal values $\Delta$log $T_1(i)$ divided by $\Delta$log $T_2(i)$, said calculating being performed repeatedly as a statistical computation after a dye injection, (d5) fourth arithmetic circuit means for calculating a specific dye concentration $C_g$ based on said $\alpha_0$ and $\alpha$ which represent changes in absorption quantities prior to and after injection of said specific dye, respectively, (d6) fifth arithmetic circuit means for calculating in accordance with the least squares method from said specific dye concentration $C_g$, a simulation curve representing calculation results which are changing with time, and (d7) sixth arithmetic circuit means for evaluating a blood plasma disappearance rate K and a T-minute retention rate R% of said specific dye based on said simulation curve, (e) output means (17, 18) connected to said central processing unit (CPU) for outputting liver function information obtained by said central processing unit, and (f) light level setting means (2) connecting an output of said central processing unit to said first and second light source means (3, 4) for adjusting light level limits for light emitted by said first and second light source means in response to signals received from said light receiving sensor means (6) prior to injection of said specific dye into a patient.

2. The apparatus of claim 1, wherein said first arithmetic means for calculating $\alpha_0$ prior to a dye injection include means for measuring $\Delta$log $T_1$ and $\Delta$log $T_2$ n times for calculating values $C_g(t)$, assuming that $\Delta$log $T_1$ and $\Delta$log $T_2$ represent values corresponding to pulse wave signals expressing intensity levels of said first light and of said second light, and wherein said third arithmetic means for calculating $\alpha$ after a dye injection includes means for forming $\alpha(t)$ from n×2 measurements by using a statistical computation based on two variables of $\Delta$log $T_1 = \alpha(t) \cdot \Delta$log $T_2$, and for obtaining:

$$C_g(t) = \beta(\alpha(t) - \alpha_0)$$

where $\beta$ represents a constant.

3. The apparatus of claim 1, wherein said simulation curve for said specific dye concentration $C_g$ calculated by said fifth arithmetic circuit means is:
$$C_g = A \cdot e^{Bt}$$

where
$C_g$: is a value of a specific dye concentration in blood,
t: is the elapsed time in minutes after injection of said specific dye,
A, B: are constants, and
wherein said sixth arithmetic circuit means for evaluating said blood plasma disappearance rate K and said T-minute retention rate R% operate on the basis of $K = -B$ and $R\% = e^{Bt}$ wherein an elapsed time (t) is T-minutes following an injection of said specific dye, for expressing an intake of said specific dye in the liver.

4. The apparatus of claim 1, wherein both said first and third arithmetic circuit means for calculating $\alpha_0$ and $\alpha$ respectively comprise means for performing a regression analysis.

* * * * *

UNITED STATES PATENT AND TRADEMARK OFFICE
CERTIFICATE OF CORRECTION

PATENT NO. : 5,154,176

DATED : October 13, 1992

INVENTOR(S) : Masahiko Kanda

It is certified that error appears in the above-identified patent and that said Letters Patent is hereby corrected as shown below:

Column 4, line 24, in equation (2) replace

"$\Delta A_1 = (E_\beta{}^1 \cdot C_\beta + E_g{}^1 \cdot c_g) \cdot \Delta D$" by --$\Delta A_1 = (E_\beta{}^1 \cdot C_\beta + E_g{}^1 \cdot C_g) \cdot \Delta D$--;

column 4, line 49, remove "(5)" from behind the equation and move --(5)-- all the way to the right of the column;

in column 4, line 59, in equation (7) replace

"$\Delta A_1 = \alpha_0 E_\beta{}^3 C_\beta \cdot \Delta D$" by --$\Delta A_1 = \alpha_0 E_\beta{}^2 C_\beta \cdot \Delta D$--.

Signed and Sealed this

Fourteenth Day of September, 1993

Attest:

BRUCE LEHMAN

*Attesting Officer*

*Commissioner of Patents and Trademarks*